United States Patent
Matsuo et al.

(10) Patent No.: US 6,916,432 B2
(45) Date of Patent: Jul. 12, 2005

(54) HAIR BLEACH COMPOSITION AND HAIR DYE COMPOSITION

(75) Inventors: Takashi Matsuo, Tokyo (JP); Hajime Miyabe, Tokyo (JP); Yutaka Shibata, Tokyo (JP); Yoshiaki Ito, Tokyo (JP); Keiji Monda, Tokyo (JP); Daisuke Misu, Tokyo (JP)

(73) Assignee: Kao Corporation, Tokyo (JP)

( * ) Notice: Subject to any disclaimer, the term of this patent is extended or adjusted under 35 U.S.C. 154(b) by 370 days.

(21) Appl. No.: 10/025,762

(22) Filed: Dec. 26, 2001

(65) Prior Publication Data

US 2002/0139957 A1 Oct. 3, 2002

(30) Foreign Application Priority Data

| Dec. 28, 2000 | (JP) | 2000-400808 |
|---|---|---|
| Dec. 28, 2000 | (JP) | 2000-400875 |
| Dec. 28, 2000 | (JP) | 2000-400876 |
| Dec. 28, 2000 | (JP) | 2000-400877 |
| Dec. 28, 2000 | (JP) | 2000-402454 |
| Feb. 5, 2001 | (JP) | 2001-027704 |
| Mar. 6, 2001 | (JP) | 2001-061696 |

(51) Int. Cl.$^7$ .............................................. C09K 3/00
(52) U.S. Cl. ......................... 252/186.1; 252/186.38; 252/186.42; 252/186.43; 252/186.44
(58) Field of Search .................. 252/186.1, 186.38, 252/186.42, 186.43, 186.44; 8/649

(56) References Cited

U.S. PATENT DOCUMENTS

| 4,330,292 A | * | 5/1982 | Bugaut et al. | 8/411 |
|---|---|---|---|---|
| 4,470,826 A | * | 9/1984 | Bugaut et al. | 8/115 |
| 5,464,552 A | * | 11/1995 | Peterson et al. | 252/186.26 |
| 5,628,991 A | | 5/1997 | Samain et al. | |
| 6,071,504 A | | 6/2000 | Kawai et al. | |
| 6,379,397 B2 | * | 4/2002 | Vidal et al. | 8/409 |

FOREIGN PATENT DOCUMENTS

| JP | 47-38974 | 10/1972 |
|---|---|---|
| JP | 54-49340 | 4/1979 |
| JP | 56-5410 | 1/1981 |
| JP | 59-106413 | 6/1984 |
| JP | 62-167504 | 7/1987 |
| JP | 1-213220 | 8/1989 |
| JP | 5-67638 | 3/1993 |
| JP | 5-97638 | 4/1993 |
| JP | 5-97838 | 4/1993 |
| JP | 5-246827 | 9/1993 |
| JP | 7-89831 | 4/1995 |
| JP | 7-196935 | 8/1995 |
| JP | 7-316029 | 12/1995 |
| JP | 7-330552 | 12/1995 |
| JP | 8-40854 | 2/1996 |
| JP | 9-100222 | 4/1997 |
| JP | 9-249537 | 9/1997 |
| JP | 9-255540 | 9/1997 |
| JP | 10-25230 | 1/1998 |
| JP | 10-45547 | 2/1998 |
| JP | 10-053970 | 2/1998 |
| JP | 10-67624 | 3/1998 |
| JP | 10-316546 | 12/1998 |
| JP | 11-29443 | 2/1999 |
| JP | 11-507067 | 6/1999 |
| JP | 11-236323 | 8/1999 |
| JP | 11-263790 | 9/1999 |
| JP | 2001-199851 | 7/2001 |
| JP | 2001-335445 | 12/2001 |
| JP | 2002-47154 | 2/2002 |

OTHER PUBLICATIONS

"Salshin Keshohln Kagaku (Modern Cosmetics Science)", first edition, pp. 114–119, The Daily Pharmaceuticals, Inc., JAPAN (Apr. 10, 1980).

"Koshohln Kagagu (Perfumery & Cometics Science)", pp. 382–392, Zaidan Hojin Japan Hair Science Association, JAPAN (Dec. 1, 1976).

* cited by examiner

*Primary Examiner*—Cephia D. Toomer
(74) *Attorney, Agent, or Firm*—Oblon, Spivak, McClelland, Maier & Neustadt, P.C.

(57) ABSTRACT

The invention provides a bleach composition or a dye composition for hair which, during use, includes a mixture of a first composition containing an alkali agent and a second composition containing an oxidizing agent, the bleach or dye composition containing (A) an organic solvent having a partition coefficient (octanol-water) (log P) at 25° C. of 0.3–6 and a molecular weight of 200 or less, in an amount of 1–70 wt. %; (B) an organic solvent having a log P of less than 0.3, in an amount of 0–8 wt. % and less than that of component (A); (C) an alkali agent in an amount of 0.1–10 wt. %; (D) an oxidizing agent in an amount of 0.1–12 wt. % as reduced to $H_2O_2$; and (E) water in an amount of 20–70 wt. %, or (A) in an amount of 1–70 wt. %; (B) in an amount of 0–8 wt. % and less than that of component (A); (C) in an amount of 0.1–10 wt. %; (D) in an amount of 0.1–12 wt. % as reduced to $H_2O_2$; (E) in an amount of 20–70 wt. %, and (F) a cationic surfactant in an amount of 0.01–10 wt. %, and has a pH of 7.5–12 after mixing of the first composition and the second composition. The bleach or dye composition provides less offensive odor; exhibit excellent hair-bleaching power and hair-dyeing power; and exhibit excellent hair-conditioning effect during and after treatment.

17 Claims, No Drawings

HAIR BLEACH COMPOSITION AND HAIR DYE COMPOSITION

BACKGROUND OF THE INVENTION

1. Field of the Invention

The present invention relates to a hair bleach composition and a hair dye composition which provide less offensive odor; exhibit excellent hair-bleaching power and hair-dyeing power; and exhibit excellent hair-conditioning effect during and after treatment.

2. Background Art

Among hair dyes, there have widely been employed two-composition-type permanent hair dyes formed of a first composition containing an alkali agent and a second composition containing an oxidizing agent. The alkali agent contained in the first composition is incorporated into the composition in order to enhance bleach effect and hair dye effect and activate the action of the oxidizing agent, to thereby promote oxidation-decomposition of melanin granules contained in the hair, leading the hair to a bright color tone. If the hair is bleached or dyed to a bright color tone as compared with the original color, the bleach or dye composition must possess sufficient bleach power, which generally varies depending on the amount of alkali. Thus, in order to bleach or dye the hair to a bright color tone, the alkali agent in particular must be provided in sufficient amount.

Conventionally, ammonia has generally been employed as the alkali agent. However, ammonia disadvantageously provides considerably unpleasant feeling during treatment because of its strongly offensive odor. Particularly, when a liquid composition is used, the ammonia odor generates easily as compared with the case where a cream-type composition is used. This has imposed great limitations on the freedom of perfume-blending into the composition.

To overcome the above problems, approaches using, instead of ammonia, organic amines generating less offensive odor have been employed (for example, see Japanese Patent Application Laid-Open (kokai) Nos. 59-106413, 1-213220, and 5-246827). However, when these approaches are followed, hair cannot be bleached to have a sufficiently bright color tone. In addition, when an organic amine is used in a large amount, problematic stimulation is readily imparted to the scalp because a comparatively high percentage thereof remains. Thus, bleaching of hair to a satisfactory bright color tone has not been attained. Furthermore, when these agents are used in hair treatment, the treated hair is damaged, resulting in hair dryness, loss of silkiness, and poor combing performance, which are also problematic.

In another approach, a portion of ammonia is substituted by another alkali agent having less odor so as to reduce the offensive odor without sacrificing satisfactory bleach effect (for example, see Japanese Patent Application Laid-Open (kokai) Nos. 9-255540, 10-25230, and 10-45547). When this approach is followed, the offensive odor is reduced to a certain extent. However, the problem cannot be solved completely, since ammonia is still required.

Japanese Patent Application Laid-Open (kokai) No. 11-29443 discloses that the combined use of an alkali agent and a type of aromatic alcohol enhances the bleaching effect and reduces the offensive odor. However, also in this case, inclusion of a certain amount of ammonia into the alkali agent is preferred, and the bleaching effect is poor if the ammonia concentration is low.

SUMMARY OF THE INVENTION

In view of the foregoing, the present inventors have carried out extensive studies, and have found that the aforementioned problems can be solved by incorporating a specific amount of a specific hydrophobic organic solvent into a hair dye and controlling the water content such that the content falls within a specific range, to thereby shift the hydrophilic/hydrophobic balance of the hair dye to the more hydrophobic side. Thus, according to a hair dye based on this finding, a hydrophilic alkali agent and a hydrophilic oxidizing agent such as hydrogen peroxide can be incorporated into the hair in a larger amount, leading to attainment of bleach effect sufficient for dyeing the hair to a bright color tone, and arbitrary perfume-blending into the hair dye can be attained without the need for masking ammonia's offensive odor, which has been a great limitation. By further adding a cationic surfactant, hair-conditioning effect can be enhanced, providing a hair dye which maintains silkiness of the hair and exhibits smooth combing performance, even when the treatment is performed by use of an alkali agent such as an organic amine.

Thus, an object of the present invention is to provide a hair bleach composition and a hair dye composition which provide less offensive odor; exhibit excellent hair-bleaching power and hair-dyeing power; and exhibit excellent hair-conditioning effect during and after treatment.

Specifically, the present invention provides a bleach composition or a dye composition for hair which, during use, comprises a mixture of a first composition containing an alkali agent and a second composition containing an oxidizing agent, the bleach or dye composition comprising the following components (A) to (E):

(A) an organic solvent having a partition coefficient (octanol-water) (log P) at 25° C. of 0.3–6 and a molecular weight of 200 or less, in an amount of 1–70 wt. %;

(B) an organic solvent having a partition coefficient (octanol-water) (log P) at 25° C. of less than 0.3, in an amount of 0–8 wt. % and less than that of component (A);

(C) an alkali agent in an amount of 0.1–10 wt. %;

(D) an oxidizing agent in an amount of 0.1–12 wt. % as reduced to hydrogen peroxide; and (E) water in an amount of 20–55 wt. %.

Moreover, the composition has a pH of 7.5–12 after mixing of the first composition and the second composition.

The present invention also provides a bleach composition or a dye composition for hair which, during use, comprises a mixture of a first composition containing an alkali agent and a second composition containing an oxidizing agent, the bleach or dye composition comprising the following components (A) to (F):

(A) an organic solvent having a partition coefficient (octanol-water) (log P) at 25° C. of 0.3–6 and a molecular weight of 200 or less, in an amount of 1–70 wt. %;

(B) an organic solvent having a partition coefficient (octanol-water) (log P) at 25° C. of less than 0.3, in an amount of 0–8 wt. % and less than that of component (A);

(C) an alkali agent in an amount of 0.1–10 wt. %;

(D) an oxidizing agent in an amount of 0.1–12 wt. % as reduced to hydrogen peroxide;

(E) water in an amount of 20–70 wt. %, and (F) a cationic surfactant in an amount of 0.01–10 wt. %.

Moreover, the composition has a pH of 7.5–12 after mixing of the first composition and the second composition.

By satisfying the above conditions, the oxidizing agent and the alkali agent can effectively function in the hair, leading to considerable enhancement of bleaching power. Thus, the amount of the alkali agent can further be reduced without deteriorating performance, to thereby mitigate the offensive odor, damage to hair, stimulation to the scalp, etc. and enhance conditioning effect. The above compositions are also effectively applied to a case in which gray hair is masked by dyeing grizzled hair to a bright color tone and, simultaneously, harmonizing gray hair to the overall hair color, which has been much in demand in recent years. In addition, portions of hair which have been chemically treated with, for example, a cold waving agent and non-treated portions can be dyed homogeneously.

DETAILED DESCRIPTION OF PREFERRED EMBODIMENTS

The organic solvent serving as component (A) must have a partition coefficient (octanol-water) (log P) at 25° C. of 0.3–6. As used herein, "log P" serves as an index of partition of a substance between an octanol phase and a water phase and is defined by the following formula:

$$\log P = \log([\text{substance}]_{Octanol}/[\text{substance}]_{Water})$$

wherein $[\text{substance}]_{Octanol}$ and $[\text{substance}]_{Water}$ represent the mol concentration of the substance in the octanol phase and that in the water phase, respectively. Examples of the calculated values are described by A. Leo, C. Hansch, and D. Elkins, in *Chemical Reviews*, vol. 71, 6 (1971). In the present invention, the partition coefficient is measured at 25° C. through a method described in "Measurement of partition coefficient (1-octanol/water) of chemical substances" <1> in "Chemical Substances according to Law Concerning the Examination and Regulation of Manufacture, etc. of Chemical substances" (revised 4th edition, edited by Kagaku Kogyo Nippo Sha).

The log P of component (A) is 0.3–6, preferably 0.5–3, more preferably 0.7–1.3, from the viewpoint of effective function in hair of the alkali agent and the oxidizing agent serving as bleach components. From the same viewpoint, the molecular weight of component (A) is 200 or less, preferably 185 or less, more preferably 160 or less. Regarding such component (A), an organic solvent having one hydroxyl group in its molecule is preferred. Specific examples include benzyl alcohol (log P (at 25° C.)=1.1; hereinafter the same applies), 2-benzyloxyethanol (1.2), ethylene glycol mono-n-butyl ether (0.8), diethylene glycol mono-n-butyl ether (0.9), n-butanol (0.8), 2-phenoxyethanol (1.2), 2-phenylethanol (1.2), 1-phenoxy-2-propanol (1.1), and cyclohexanol (1.2). Of these, benzyl alcohol and 2-benzyloxyethanol are preferred.

The solvent serving as component (A) may be used in combination of two or more species, and from the viewpoint of satisfactory bleaching or dyeing effect, the total content is 1–70 wt. % of the entire composition (i.e., the first and second compositions in the case of two-composition type composition; or the first, second, and third compositions in the case of three-composition type composition; the same applies hereinafter), preferably 1–50 wt. %, more preferably 3–40 wt. %, particularly preferably 5–25 wt. %.

Into the composition of the present invention, an organic solvent having a partition coefficient (octanol-water) (log P) at 25° C. of less than 0.3 may be incorporated as component (B). Examples of the organic solvents serving as component (B) include lower alkanols, C2–C6 polyols, glycol mono-lower-alkyl ethers, diglycol mono-lower-alkyl ethers, and N-lower-alkylpyrrolidones. The term "lower" refers to the number of carbon atoms being 3 or less.

Specific examples include lower alkanols such as ethanol (log P (at 25° C.)=–0.3) and isopropanol (0.1); lower polyols such as ethylene glycol (–1.4), propylene glycol (–1.1), 1,3-butanediol (–1.4), diethylene glycol (–1.3), hexylene glycol (–0.7), and glycerin (–2.2); glycol mono-lower-alkyl ethers such as 2-methoxyethanol (–0.7) and 2-ethoxyethanol (–0.2); diglycol mono-lower-alkyl ethers such as methoxydiglycol (–0.7) and ethoxydiglycol (–0.2); and N-lower-alkylpyrrolidones such as N-methylpyrrolidone (–0.5) and N-ethylpyrrolidone (–0.2).

In order to improve bleaching effect or dyeing effect, component (B) is incorporated in an amount of 8 wt. % or less into the entire composition and less than the amount of component (A), in order to effectively cause the alkali agent and the oxidizing agent to act in the hair. When the amount of component (B) is excessively high, the hydrophilic/hydrophobic balance is shifted to the hydrophilic side during mixing of the first composition and the second composition, which is contrary to the purpose of the present invention. The amount of component (B) is preferably 0–5 wt. % based on the entire composition, particularly preferably 0–2 wt. %.

The alkali agent serving as component (C) may be a compound other than ammonia. Examples thereof include alkanolamines such as monoethanolamine, monoisopropanolamine, 2-amino-2-methylpropanol, and 2-aminobutanol; and guanidinium salts such as guanidinium carbonate. Of these, alkanolamines, inter alia monoethanolamine, are preferred. These alkali agents included in component (C) may be used in combination of two or more species, and the total content is 0.1–10 wt. % based on the entire composition, preferably 0.5–5 wt. %, more particularly 1–3 wt. %, from the viewpoints of sufficient bleach/dye effect and low stimulation to the scalp. The composition of the present invention provides satisfactory bleach/dye effect even when the composition contains no ammonia serving as an alkali agent. Such a composition containing no ammonia is preferred, since the composition generates no offensive odor attributable to ammonia and provides no unfavorable sensation during use. If ammonia is used, the bleach/dye effect can be further enhanced. The concentration of ammonia is controlled to 0–3 wt. % based on the entire composition, preferably 0–1 wt. %, more particularly 0–0.5 wt. %, so as to attain arbitrary perfume-blending into the composition without the need for the masking of ammonia's offensive odor. As used herein, the term "ammonia" encompasses ammonium salts such as ammonium carbonate, which generate ammonia by adjusting pH of the hair dye composition.

Examples of oxidizing agents serving as component (D) include hydrogen peroxide, peroxyurea, peroxymelamine, sodium perborate, potassium perborate, sodium percarbonate, and potassium percarbonate, with hydrogen peroxide being particularly preferred. These oxidizing agents may be used in combination of two or more species, and the total content as reduced to hydrogen peroxide is 0.1–12 wt. % based on the entire composition, preferably 1–9 wt. %, particularly preferably 2–6 wt. %, from the viewpoints of sufficient bleach/dye effect and low stimulation to the scalp.

In addition to the oxidizing agent of the aforementioned component (D), a persulfate salt may further be incorporated into the composition of the present invention. Examples of the persulfate salt include alkali metal persulfate salts such as sodium persulfate and potassium persulfate; and ammonium persulfate. Of these, sodium persulfate, potassium persulfate, and ammonium persulfate are preferred. The persulfate salt content may be 1–30 wt. % based on the entire composition, particularly preferably 5–15 wt. %, from the viewpoints of bleach power and less damage to the hair.

When the composition contains a cationic surfactant serving as component (F), the water (serving as component (E)) content of the composition is controlled to 20–70 wt. % based on the entire composition. In the case in which the composition is used mainly for the purpose of bleaching hair, the water content is preferably 25–55 wt. %, particularly preferably 30–55 wt. %, whereas in the case in which the composition is used mainly for the purpose of dyeing hair, the water content is preferably 30–65 wt. %, particularly preferably 40–65 wt. %. But the cationic surfactant serving as component (F) is not always necessary to the composition, in which case the water (serving as component (E)) content is controlled to 20–55 wt. % based on the entire composition. In the case in which the composition is used mainly for the purpose of bleaching hair, the water content is preferably 25–55 wt. %, particularly preferably 30–50 wt. %, whereas in the case in which the composition is used mainly for the purpose of dyeing hair, the water content is preferably 30–55 wt. %, particularly preferably 40–55 wt. %. In the case where emphasis is placed on hair bleaching, a smaller water content is advantageous, since a hydrophilic alkali agent and a hydrophilic oxidizing agent such as hydrogen peroxide can be incorporated into the hair in a larger amount by means of shifting the hydrophilic/hydrophobic balance of the composition to the hydrophobic side. In contrast, in the case where emphasis is placed on hair dyeing, a water content greater than that employed in the case of hair bleaching is advantageous, since a dye—a comparatively hydrophobic component—must be distributed into the hair while the hydrophilic/hydrophobic balance of the composition is shifted to the hydrophobic side as compared with the case of a conventional composition.

The composition of the present invention may contain a cationic surfactant serving as component (F). Any cationic surfactant which is incorporated into rinses or softeners can be used as the cationic surfactant, and examples thereof include those represented by the following formula (1)

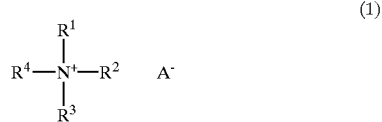

wherein each of $R^1$, $R^2$, $R^3$, and $R^4$ represents an optionally substituted hydrocarbon group; preferably, at least one of $R^1$ and $R^2$ has 8–36 carbon atoms and the remaining one has 1–7 carbon atoms, or $R^3$ and $R^4$ may form together, with the adjacent nitrogen atom, a 5–7-membered ring which may have a C1–C4 alkyl substituent and a nitrogen atom, an oxygen atom, or a sulfur atom serving as a hetero atom other than the above nitrogen atom; and $A^-$ represents an anion.

Examples of the hydrocarbon groups represented by $R^1$ to $R^4$ include linear or branched alkyl groups, linear or branched alkenyl groups, aryl groups, and aralkyl groups. Examples of the substituent include a hydroxyl group, an alkoxy group, an aryloxy group, an epoxy group, an amino group, a mono- or dialkylamino group, a trialkylammonium group, a fatty acid amido group, and a fatty acid ester group. Examples of rings which may be formed include a morpholine ring, an imidazoline ring, a piperazine ring, a piperidine ring, and a pyrrolidine ring.

Examples of the anion represented by $A^-$ include a chloride ion, a bromide ion, an iodide ion, a methylsulfate ion, an ethylsulfate ion, an acetate ion, a phosphate ion, a sulfate ion, a lactate ion, and a saccharin-derived anion.

Specific examples of component (F) include cetyltrimethylammonium chloride, stearyltrimethylammonium chloride, isostearyltrimethylammonium chloride, lauryltrimethylammonium chloride, behenyltrimethylammonium chloride, octadecyltrimethylammonium chloride, cocoyltriinethylammonium chloride, cetyltrimethylammonium bromide, stearyltrimethylammonium bromide, lauryltrimethylammonium bromide, isostearyllauryldimethylammonium chloride, dicetyldimethylammonium chloride, distearyldimethylammonium chloride, dicocoyldimethylammonium chloride, γ-gluconamidopropyldimethylhydroxyethylammonium chloride, di[polyoxyethylene(2)]oleylmethylammonium chloride, dodecyldimethylethylammonium chloride, octyldihydroxyethylmethylammonium chloride, tri[polyoxyethylene(5)]stearylammonium chloride, polyoxypropylenemethyldiethylammonium chloride, lauryldimethyl(ethylbenzyl)ammonium chloride, behenamidopropyl-N,N-dimethyl-N-(2,3-dihydroxypropyl) ammonium chloride, tallowdimethylammoniopropyltrimethylammonium dichloride, and benzalconium chloride.

Regarding the aforementioned cationic surfactant, those represented by formula (1) in which at least one of $R^1$ and $R^2$ is a C8–C30 alkyl group or alkenyl group or a fatty acid amidoalkyl group and the remaining group is a methyl group are preferred.

The component (F) content may be controlled to 0.01–10 wt. % based on the entire composition, preferably 0.1–5 wt. %, particularly preferably 0.5–3 wt. %, in view of bleach/dye effect and conditioning effect.

Any combination of the above-recited elements of component (A) and those of component (F) is preferred. Of these, particularly preferred are combinations of (A) benzyl alcohol and (F) stearyltrimethylammonium chloride; (A) 2-benzyloxyethanol and (F) stearyltrimethylammonium chloride; (A) n-butanol and (F) stearyltrimethylammonium chloride; (A) ethylene glycol monon-butyl ether and (F) stearyltrimethylammonium chloride; (A) benzyl alcohol and (F) dicetyldimethylammonium chloride; (A) 2-benzyloxyethanol and (F) dicetyldimethylammonium chloride; (A) n-butanol and (F) dicetyldimethylammonium chloride; and (A) ethylene glycol mono-n-butyl ether and (F) dicetyldimethylammonium chloride.

When the hair dye composition of the present invention is used in order to simply bleach hair, no oxidation-type dye intermediate or direct dye is incorporated into the composition, which thereby serves as a hair bleach. However, in order to dye hair, the composition further contains an oxidation-type dye intermediate serving as component (G) or a direct dye serving as component (H).

Regarding component (G), known color developing substances and coupling substances which are generally employed in hair dyes can be used. Examples of color developing substances include p-phenylenediamine, toluene-2,5-diamine, 2-chloro-p-phenylenediamine, N-methoxyethyl-p-phenylenediamine, N,N-bis(2-hydroxyethyl)-p-phenylenediamine, 2-(2-hydroxyethyl)-p-phenylenediamine, 2,6-dimethyl-p-phenylenediamine, 4,4'-diaminodiphenylamine, 1,3-bis[N-(2-hydroxyethyl)-N-(4-aminophenyl)amino]-2-propanol, PEG-3,3,2'-p-phenylenediamine, p-aminophenol, p-methylaminophenol, 3-methyl-4-aminophenol, 2-aminomethyl-4-aminophenol, 2-(2-hydroxyethylaminomethyl)-4-aminophenol, o-aminophenol, 2-amino-5-methylphenol, 2-amino-6-methylphenol, 2-amino-5-acetamidophenol, 3,4- diaminobenzoic acid, 5-aminosalicylic acid, 2,4,5,6-tetraaminopyrimidine, 2,5,6-triamino-4-hydroxypyrimidine, 4,5-diamino-1-(4'-chlorobenzyl)pyrazole, 4,5-diamino-1-hydroxyethylpyrazole, and salts thereof.

Examples of the coupling substances include m-phenylenediamine, 2,4-diaminophenoxyethanol, 2-amino-4-(2-hydroxyethylamino)anisole, 2,4-diamino-5-methylphenetole, 2,4-diamino-5-(2-hydroxyethoxy)toluene, 2,4-dimethoxy-1,3-diaminobenzene, 2,6-bis(2-hydroxyethylamino)toluene, 2,4-diamino-5-fluorotoluene, 1,3-bis(2,4-diaminophenoxy)propane, m-aminophenol, 2-methyl-5-aminophenol, 2-methyl-5-(2-hydroxyethylamino)phenol, 2,4-dichloro-3-aminophenol, 2-chloro-3-amino-6-methylphenol, 2-methyl-4-chloro-5-aminophenol, N-cyclopentyl-m-aminophenol, 2-methyl-4-methoxy-5-(2-hydroxyethylamino)phenol, 2-methyl-4-fluoro-5-aminophenol, resorcin, 2-methylresorcin, 4-chlororesorcin, 1-naphthol, 1,5-dihydroxynaphthalene, 1,7-dihydroxynaphthalene, 2,7-dihydroxynaphthalene, 2-isopropyl-5-methylphenol, 4-hydroxyindole, 5-hydroxyindole, 6-hydroxyindole, 7-hydroxyindole, 6-hydroxybenzomorpholine, 3,4-methylenedioxyphenol, 2-bromo-4,5-methylenedioxyphenol, 3,4-methylenecdioxyaniline, 1-(2-hydroxyethyl)amino-3,4-methylenecdioxybenzene, 2,6-dihydroxy-3,4-dimethylpyridine, 2,6-dimethoxy-3,5-diaminopyridine, 2,3-diamino-6-methoxypyridine, 2-methylamino-3-amino-6-methoxypyridine, 2-amino-3-hydroxypyridine, 2,6-diaminopyridine, and salts thereof.

These color developing substances and coupling substances may be used, respectively, in combination of two or more species. The amount of respective substances may be controlled to 0.01–5 wt. % based on the entire composition, particularly preferably 0.1–4 wt. %.

Regarding component (H), known dyes employable in hair dyes such as acid dyes, basic dyes, disperse dyes, and reactive dyes may be used. Examples of the acid dyes include Acid Red 27 (C.I. 16185), Acid Red 51 (C.I. 45430), Acid Red 18 (C.I. 16255), Acid Red 92 (C.I. 45410), Acid Red 94 (C.I. 45440), Acid Red 52 (C.I. 45100), Acid Yellow 23 (C.I. 19140), Food Yellow 3 (C.I. 15985), Food Green 3 (C.I. 42053), Food Blue 2 (C.I. 42090), Acid Blue 74 (C.I. 73015), Pigment Red 57-1 (C.I. 15850), Acid Red 33 (C.I. 17200), Acid Red 87 (C.I. 45380), Acid Orange 7 (C.I. 15510), Acid Red 95 (C.I. 45425), Acid Yellow 73 (C.I. 45350), Acid Yellow 3 (C.I. 47005), Acid Green 25 (C.I. 61570), Solvent Green 7 (C.I. 59040), Acid Green 5 (C.I. 42095), Acid Blue 5 (C.I. 42052), Acid Blue 9 (C.I. 42090), Acid Orange 24 (C.I. 20170), Acid Violet 9 (C.I. 45190), Food Red 6 (C.I. 16155), Acid Red 26 (C.I. 16150), Food Red 1 (C.I. 14700), Acid Red 88 (C.I. 15620), Acid Orange 20 (C.I. 14600), Acid Yellow 40 (C.I. 18950), Acid Yellow 1 (C.I. 10316), Acid Yellow 36 (C.I. 13065), Acid Yellow 11 (C.I. 18820), Acid Green 1 (C.I. 10020), Acid Green 3 (C.I. 42085), Acid Violet 43 (C.I. 60730), Acid Black 1 (C.I. 20470), Acid Black 52 (C.I. 15711), Acid Blue 1 (C.I. 42045), Acid Blue 3 (C.I. 42051), Acid Blue 62 (C.I. 62045), Acid Brown 13 (C.I. 10410), Acid Green 50 (C.I. 44090), Acid Orange 3 (C.I. 10385), Acid Orange 6 (C.I. 14270), Acid Red 14 (C.I. 14720), Acid Red 35 (C.I. 18065), Acid Red 73 (C.I. 27290), Acid Red 184 (C.I. 15685), and Brilliant Black 1 (C.I. 28440).

Examples of the basic dyes include Basic Blue 7 (C.I. 42595), Basic Blue 16 (C.I. 12210), Basic Blue 22 (C.I. 61512), Basic Blue 26 (C.I. 44045), Basic Blue 99 (C.I. 56059), Basic Blue 117, Basic Violet 10 (C.I. 45170), Basic Violet 14 (C.I. 42515), Basic Brown 16 (C.I. 12250), Basic Brown 17 (C.I. 12251), Basic Red 2 (C.I. 50240), Basic Red 12 (C.I. 48070), Basic Red 22 (C.I. 11055), Basic Red 51, Basic Red 76 (C.I. 12245), Basic Red 118 (C.I. 12251:1), Basic Orange 31, Basic Yellow 28 (C.I. 48054), Basic Yellow 57 (C.I. 12719), Basic Yellow 87, and Basic Black 2 (C.I. 11825); basic dyes containing a quaternary nitrogen atom in the side chain of an aromatic ring skeleton, the dyes disclosed in, for example, Japanese Patent Publication (kokoku) No. 58-2204 and Japanese Patent Application Laid-Open (kokai) No. 9-118832; and basic dyes disclosed in, for example, Japanese Kohyo Patent Publication No. 10-502946 and Japanese Patent Application Laid-Open (kokai) Nos. 10-182379 and 11-349457.

Examples of the direct dyes other than acid dyes and basic dyes include 2-amino-3-nitrophenol, 2-amino-4-nitrophenol, 2-amino-5-nitrophenol, 4-amino-3-nitrophenol, 2-amino-6-chloro-4-nitrophenol, 4-hydroxypropylamino-3-nitrophenol, 3-nitro-p-hydroxyethylaminophenol, 2-nitro-p-phenylenediamine, 4-nitro-o-phenylenediamine, 4-nitro-m-phenylenediamine, 6-nitro-o-toluidine, 6-nitro-p-toluidine, hydroxyethyl-2-nitro-p-toluidine, N,N'-bis(2-hydroxyethyl)-2-nitro-p-phenylenediamine, 2-chloro-5-nitro-N-hydroxyethyl-p-phenylenediamine, 2-nitro-5-glycerylmethylaniline, 3-methylamino-4-nitrophenoxyethanol, N-ethyl-3-nitro-PABA, picramic acid, 2-hydroxyethylpicramic acid, 4-nitrophenylaminoethylurea, Solvent Violet 13 (C.I. 60725), Solvent Yellow 44 (C.I. 56200), Disperse Red 17 (C.I. 11210), Disperse Violet 1 (C.I. 61100), Disperse Violet 4 (C.I. 61105), Disperse Blue 3 (C.I. 61505), Disperse Blue 7 (C.I. 62500), HC Blue No.2, HC Blue No.8, HC Orange No.1, HC Orange No.2, HC Red No.1, HC Red No.3, HC Red No.7, HC Red No.8, HC Red No.10, HC Red No.11, HC Red No.13, HC Red No.16, HC Violet No.2, HC Yellow No.2, HC Yellow No.5, HC Yellow No.6, HC Yellow No.7, HC Yellow No.9, and HC Yellow No.12.

These direct dyes may be used in combination of two or more species, and the total amount may be 0.001–5 wt. % based on the entire composition, particularly preferably 0.01–4 wt. %. Furthermore, an oxidation-type dye intermediate and a direct dye may be used in combination.

The composition of the present invention preferably contains a higher aliphatic alcohol serving as component (I). As used herein, the term "higher aliphatic alcohol" refers to a saturated or unsaturated C12–C22 linear or branched monohydric alcohol. Examples include myristyl alcohol, cetyl alcohol, stearyl alcohol, and oleyl alcohol. Of these, cetyl alcohol, oleyl alcohol, and similar alcohols are preferred. The component (I) content may be 0.1–20 wt. % based on the entire composition, particularly preferably 0.2–10 wt. %.

The composition of the present invention preferably contains a specific polyoxyalkylene compound serving as component (J). Examples of the polyoxyalkylene compound include polyalkylene glycols having a total polycondensation number of C2–C4 oxyalkylene groups of 4 or more; polyalkylene glycol alkyl (C1–C4) ethers; polyalkylene glycol glyceryl ethers; polyalkylene glycol pentaerythritol alkylene glycol ethers; polyalkylene glycoltrimethylolpropane ethers; and polyalkylene glycol alkylene glycol ethers. The oxyethylene groups, oxypropylene groups, and oxybutylene groups of any of these compound are optionally added in a block or random manner. preferably, these compounds are homogeneously dissolved or dispersed in the hair dye composition.

Specific examples of component (J) include polyethylene glycol, polypropylene glycol, polybutylene glycol, and polyoxyethylene polyoxypropylene glycol. The polycondensation number of these polyalkylene glycols may be 4–500, preferably 5–100, particularly preferably 6–60.

The polyalkylene glycol alkyl (C1–C4) ethers are ethers formed from any of the aforementioned polyalkylene glycols and any of alcohols such as methanol, ethanol, n-propanol, and n-butanol. Specific examples include polyethylene glycol monomethyl ether, polypropylene glycol mono-n-butyl ether, and polyoxyethylene polyoxypropylene glycol mono-n-butyl ether.

The polyalkylene glycol glyceryl ethers are monoethers formed from any of the aforementioned polyalkylene glycols and glycerin. Specific examples include polyethylene glycol glyceryl ether, polypropylene glycol glyceryl ether, polypropylene glycol diglyceryl ether, and polyoxyethylene polyoxypropylene glycol glyceryl ether.

The polyalkylene glycol pentaerythritol ethers are ethers formed from any of the aforementioned polyalkylene glycols and pentaerythritol. Specific examples include polyoxyethylene pentaerythritol ether.

The polyalkylene glycol trimethylolpropane ethers are ethers formed from any of the aforementioned polyalkylene glycols and trimethylolpropane. Specific examples include polyoxyetlhylene polyoxypropylene trimethylolpropane ether.

The polyalkylene glycol alkylene glycol ethers are ethers formed from any of the aforementioned polyalkylene glycols and alkylene (C3–C6) glycol. Specific examples include butanediol di(polypropylene glycol) ether and propylene glycol (polyethylene glycol) ether.

Among these polyoxyalkylene compounds, polyoxyalkylene glycols and polyoxyalkylene glycol alkyl (C1–C4) ethers are preferred, with polypropylene glycol being particularly preferred.

These species may be used in combination of two or more species. They are effective for incorporating a hydrophilic alkali agent and a hydrophilic oxidizing agent such as hydrogen peroxide into hair in a larger amount in the presence of component (A), and the total content may be 0.1–20 wt. % based on the entire composition, particularly preferably 0.5–10 wt. %.

The composition of the present invention preferably contains at least two species of nonionic surfactants having different HLB values; i.e., a hydrophilic nonionic surfactant having an HLB 10–20 (component (K)) and an oleophilic nonionic surfactant having an HLB 1–10 (component (L)), the surfactants being incorporated into the first composition and/or the second composition.

Examples of the hydrophilic nonionic surfactant serving as component (K) include polyoxyethylene alkyl ethers such as polyoxyethylene octyldodecyl ether, polyoxyethylene oleyl ether, polyoxyethylene tridecyl ether, polyoxyethylene lauryl ether, and polyoxyethylene isostearyl ether; and alkyl glycosides, these compounds having an HLB of 10–20.

Examples of the oleophilic nonionic surfactant serving as component (L) include the above polyoxyethylene alkyl ethers, but having an HLB of 1–10; and polyoxyethylene polypropylene alkyl ethers, alkyl glyceryl ethers, alkyl glyceryl pentaerythritol ethers, alkyl diglyceryl ethers, and alkyl triglyceryl ethers, these compounds having an HLB of 1–10. Particularly, isostearyl glyceryl ether, isostearyl diglyceryl ether, and isostearyl pentaerythryl glyceryl ether are preferred.

Preferably, components (K) and (L) are added to the first composition and/or the second composition such that the weighted average HLB on the basis of content attains 8–12 and the total content is 2–70 wt. %, particularly preferably 9–11 and 10–50 wt. %, after completion of mixing the first and second compositions, since, under the above conditions, the state of either or both of the first and second compositions is a liquid, and liquid crystals are formed during mixing of the compositions, to thereby increase viscosity, leading to prevention of running of the composition during application of the composition. In a more preferred embodiment, components (K) and (L) are added in the first composition in the above amounts, and the resultant mixture is mixed with water-rich second composition, to thereby form liquid crystals upon mixing. The HLB value used herein refers to an HLB value obtained in accordance with Griffin's method. The term "liquid" with regard to the first and second compositions refers to a state where viscosity is 3000 mPa·s or less, preferably 1000 mPa·s or less, as measured at 25° C. by use of a model B viscometer (BM model, produced by Toki Sangyo Co., Ltd.). Preferably, after completion of mixing of the two compositions, the viscosity is 3000 mPa·s or higher, particularly 5000 mPa·s or higher. Herein, the viscosity is a value measured by use of Rotor No. 3 under rotation at 12 rpm for one minute.

The mixing ratio (by weight) of the first composition containing an alkali agent to the second composition containing an oxidizing agent, for yielding the composition of the present invention, is preferably 1:0.5 (first second) to 1:3, for practical reasons.

Preferably, the first composition has a pH of 8–12 at 25° C., and the second composition has a pH of 2–5. The composition obtained by mixing the first and second compositions has a pH of 7.5–12. However, the pH is preferably 8–11, from the viewpoints of bleach/dye effect and low stimulation to the skin.

The composition of the present invention may contain a perfume. The hair dye composition of the present invention attains satisfactory bleach/dye effect without containing ammonia as an alkali agent. Thus, the composition is advantageous in that arbitrary perfume-blending into the hair dye can be attained by virtue of no requirement for masking of ammonia's offensive odor, and fruity aroma, floral aroma, etc. are easily imparted to the composition.

In a manner similar to currently widely used oxidation-type hair bleaches or hair dyes, the composition of the present invention is provided as a two-composition-type; i.e., the composition includes the first composition containing an alkali agent and the second composition containing an oxidizing agent. The form of the first and second compositions may be liquid, milky lotion, cream, gel, paste, or mousse. Alternatively, the composition is formed into an aerosol. When a persulfate salt is employed as an additional oxidizing agent, the composition is provided preferably as a three-composition-type, including the aforementioned first and second compositions and a third composition containing a persulfate salt. The third composition containing a persulfates may be formed into powder, granules, and grains.

When hair is subjected to bleach or dye treatment by use of the composition of the present invention, the following procedure is employed. Specifically, the first and second compositions and an optional third composition according to the present invention are mixed together, and the resultant mixture is applied to hair at 15–45° C. The treatment is effected for 1–50 minutes, preferably 3–30 minutes. After termination of treatment, the treated hair is washed and dried.

EXAMPLES

Hair bleaches and hair dyes prepared in the following Examples were evaluated in the manner described below.

Specifically, hair which had not been chemically treated was collected from one Japanese person, and two hair samples, each having a weight of 10 g, were prepared. To one hair sample, each product (7 g) according to the present invention was uniformly applied. The sample was allowed to stand in a thermostat bath at 30° C. for 15 minutes, and rinsed with warm water (30° C.). The sample was further shampooed, rinsed, and dried. The thus-treated hair sample was compared with the other, untreated hair sample, thereby evaluating bleach level or dye level after this treatment.

Example 1

An oxidation-type hair bleach having the following composition was prepared, and its bleaching effect was evaluated.

| | (wt. %) |
|---|---|
| First composition | |
| 2-benzyloxyethanol | 10 |
| ethanol | 3 |
| monoethanolamine | 6 |
| oleyl alcohol | 2 |
| polyoxyethylene(20) octyldodecyl ether | 18 |
| polyoxyethylene(9) oleyl ether | 6 |
| polyoxyethylene(3) triclecyl ether | 15 |
| polyethylene glycol 400 | 8 |
| liquid paraffin | 6 |
| perfume | 0.4 |
| purified water | 25.6 |
| Total | 100 |
| Second composition | |
| 35 wt. % aqueous hydrogen peroxide | 17 |
| polyoxyethylene(9) oleyl ether | 25 |
| oleyl alcohol | 15 |
| 8-quinolinol sulfate | 0.04 |
| 75 wt. % phosphoric acid | 0.02 |
| purified water | 42.94 |
| Total | 100 |

The first composition and the second composition were mixed at a ratio of 1:1.5 (by weight), to thereby prepare a composition. When used, the composition provided a weak offensive odor and excellent bleach power.

Example 2

An oxidation-type hair bleach having the following composition was prepared, and its bleaching effect was evaluated.

| | (wt. %) |
|---|---|
| First composition | |
| benzyl alcohol | 16 |
| ethanol | 5 |
| 28 wt. % aqueous ammonia | 3 |
| oleyl alcohol | 2 |
| polyoxyethylene(20) octyldodecyl ether | 18 |
| polyoxyethylene(9) oleyl ether | 6 |
| polyoxyethylene(3) tridecyl ether | 15 |
| polyoxyethylene(2) sodium lauryl sulfate | 2.5 |
| polypropylene glycol 400 | 12 |
| perfume | 0.6 |
| purified water | 19.9 |
| Total | 100 |

| -continued | |
|---|---|
| | (wt. %) |
| Second composition | |
| 35 wt. % aqueous hydrogen peroxide | 17 |
| polyoxyethylene(9) oleyl ether | 25 |
| oleyl alcohol | 15 |
| 8-quinolinol sulfate | 0.04 |
| 75 wt. % phosphoric acid | 0.02 |
| purified water | 42.94 |
| Total | 100 |

The first composition and the second composition were mixed at a ratio of 1:1 (by weight), to thereby prepare a composition. When used, the composition provided a weak offensive odor and excellent bleach power.

Example 3

An oxidation-type hair dye having the following composition was prepared, and its dyeing effect was evaluated.

| | (wt. %) |
|---|---|
| First composition | |
| p-aminophenol | 0.9 |
| p-amino-o-cresol | 1 |
| 2-benzyloxyethanol | 24 |
| propylene glycol | 4.5 |
| monoethanolamine | 6 |
| oleyl alcohol | 3 |
| polyoxyethylene(20) octyldodecyl ether | 21 |
| polyoxyethylene(3) tridecyl ether | 18 |
| polyoxyethylene(2) sodium lauryl sulfate | 2.5 |
| perfume | 0.5 |
| purified water | 18.6 |
| Total | 100 |
| Second composition | |
| 35 wt. % aqueous hydrogen peroxide | 17 |
| cetanol | 3 |
| polyoxyethylene(2) cetyl ether | 3 |
| polyoxyethylene(2) sodium lauryl sulfate | 1.5 |
| amino-modified silicone emulsion (40 wt. %) * | 2 |
| 8-quinolinol sulfate | 0.04 |
| 75 wt. % phosphoric acid | 0.03 |
| purified water | 73.43 |
| Total | 100 |

* SM8702C (product of Toray Dow Corning Silicone)

The first composition and the second composition were mixed at a ratio of 1:1 (by weight), to thereby prepare a composition. When used, the composition provided a weak offensive odor and favorably dyed the hair sample to a bright color tone.

Example 4

An oxidation-type hair dye having the following composition was prepared, and its dyeing effect was evaluated.

| | (wt. %) |
|---|---|
| First composition | |
| toluene-2, 5-diamine | 1.5 |
| resorcin | 1.35 |

-continued

| | (wt. %) |
|---|---|
| Basic Yellow 87 | 0.3 |
| ethylene glycol mono-n-butyl ether | 20 |
| monoethanolamine | 6 |
| 28 wt. % aqueous ammonia | 5 |
| oleyl alcohol | 4 |
| polyoxyethylene(20) octyldodecyl ether | 17 |
| polyoxyethylene(9) oleyl ether | 4 |
| polyoxyethylene(3) tridecyl ether | 17 |
| polypropylene glycol 400 | 7 |
| Na sulfite anhydrate | 0.6 |
| 4Na edetate dihydrate | 0.1 |
| perfume | 0.5 |
| purified water | 15.65 |
| Total | 100 |
| Second composition | |
| 35 wt. % aqueous hydrogen peroxide | 17 |
| cetanol | 3 |
| polyoxyethylene(2) cetyl ether | 2 |
| amino-modified silicone emulsion (40 wt. %) * | 1 |
| 8-quinolinol sulfate | 0.04 |
| 75 wt. % phosphoric acid | 0.03 |
| purified water | 76.93 |
| Total | 100 |

* Same as Example 3

The first composition and the second composition were mixed at a ratio of 1:1 (by weight), to thereby prepare a composition. When used, the composition provided a weak offensive odor and favorably dyed the hair sample to a bright color tone.

Example 5

An oxidation-type hair dye having the following composition was prepared, and its dyeing effect was evaluated.

| | (wt. %) |
|---|---|
| First composition | |
| Basic Red 12 | 0.4 |
| 2-benzyloxyethanol | 10 |
| ethanol | 3 |
| monoethanolamine | 6 |
| oleyl alcohol | 2 |
| polyoxyethylene(20) octyldodecyl ether | 18 |
| polyoxyethylene(9) oleyl ether | 6 |
| polyoxyethylene(3) tridecyl ether | 15 |
| polyethylene glycol 400 | 8 |
| liquid paraffin | 6 |
| perfume | 0.4 |
| purified water | 25.2 |
| Total | 100 |
| Second composition | |
| 35 wt. % aqueous hydrogen peroxide | 17 |
| polyoxyethylene(9) oleyl ether | 16 |
| oleyl alcohol | 13 |
| 8-quinolinol sulfate | 0.04 |
| 75 wt. % phosphoric acid | 0.02 |
| purified water | 53.94 |
| Total | 100 |

The first composition and the second composition were mixed at a ratio of 1:1.5 (by weight), to thereby prepare a composition. When used, the composition provided a weak offensive odor and favorably dyed the hair sample to a bright color tone.

Example 6

An oxidation-type hair bleach having the following composition was prepared, and its bleaching effect was evaluated.

| | (wt. %) |
|---|---|
| First composition | |
| benzyl alcohol | 10 |
| ethanol | 3 |
| monoethanolamine | 6 |
| oleyl alcohol | 2 |
| polyoxyethylene(20) octyldodecyl ether | 18 |
| polyoxyethylene(9) oleyl ether | 6 |
| polyoxyethylene(3) tridecyl ether | 15 |
| stearyltrimethylammonium chloride | 2 |
| polyethylene glycol 400 | 8 |
| liquid paraffin | 6 |
| perfume | 0.4 |
| purified water | 23.6 |
| Total | 100 |
| Second composition | |
| aqueous hydrogen peroxide(35%) | 17 |
| polyoxyethylene(9) oleyl ether | 25 |
| oleyl alcohol | 15 |
| 8-quinolinol sulfate | 0.04 |
| 75 wt. % phosphoric acid | 0.02 |
| purified water | 42.94 |
| Total | 100 |

The first composition and the second composition were mixed at a ratio of 1:1.5 (by weight), to thereby prepare a composition. When used, the composition provided a weak offensive odor and excellent bleach power. The texture of the hair sample after having undergone bleaching was smooth.

Example 7

An oxidation-type hair bleach having the following composition was prepared, and its bleaching effect was evaluated.

| | (wt. %) |
|---|---|
| First composition | |
| ethylene glycol mono-n-butyl ether | 16 |
| ethanol | 5 |
| 28 wt. % aqueous ammonia | 3 |
| oleyl alcohol | 2 |
| polyoxyethylene(20) octyldodecyl ether | 18 |
| polyoxyethylene(9) oleyl ether | 6 |
| polyoxyethylene(3) tridecyl ether | 15 |
| stearyltrimethylammmonium chloride | 2.5 |
| polypropylene glycol 400 | 12 |
| perfume | 0.6 |
| purified water | 19.9 |
| Total | 100 |
| Second composition | |
| 35 wt. % aqueous hydrogen peroxide | 17 |
| polyoxyethylene(9) oleyl ether | 25 |
| oleyl alcohol | 15 |
| 8-quinolinol sulfate | 0.04 |
| 75 wt. % phosphoric acid | 0.02 |
| purified water | 42.94 |
| Total | 100 |

The first composition and the second composition were mixed at a ratio of 1:1 (by weight), to thereby prepare a composition. When used, the composition provided a weak offensive odor and excellent bleach power. The texture of the hair sample after having undergone bleaching was smooth.

Example 8

An oxidation-type hair bleach having the following composition was prepared, and its bleaching effect was evaluated.

|  | (wt. %) |
| --- | --- |
| First composition | |
| 2-benzyloxyethanol | 24 |
| propylene glycol | 4.5 |
| monoethanolamine | 5 |
| 28 wt. % aqueous ammonia | 2 |
| oleyl alcohol | 3 |
| polyoxyethylene(20) octyldodecyl ether | 21 |
| polyoxyethylene(3) tridecyl ether | 18 |
| stearyltrimethylammonium chloride | 2.5 |
| perfume | 0.5 |
| purified water | 19.5 |
| Total | 100 |
| Second composition | |
| 35 wt. % aqueous hydrogen peroxide | 17 |
| cetyl alcohol | 3 |
| polyoxyethylene(2) cetyl ether | 3 |
| stearyltrimethylammonium chloride | 1.5 |
| amino-modified silicone emulsion (40 wt. %) * | 2 |
| 8-quinolinol sulfate | 0.04 |
| 75 wt. % phosphoric acid | 0.03 |
| purified water | 73.43 |
| Total | 100 |

* Same as Example 3

The first composition and the second composition were mixed at a ratio of 1:1 (by weight), to thereby prepare a composition. When used, the composition provided a weak offensive odor and excellent bleach power. The texture of the hair sample after having undergone bleaching was smooth.

Example 9

An oxidation-type hair dye having the following composition was prepared, and its dyeing effect was evaluated.

|  | (wt.%) |
| --- | --- |
| First composition | |
| p-aminophenol | 0.9 |
| p-amino-o-cresol | 1 |
| ethylene glycol mono-n-butyl ether | 20 |
| monoethanolamine | 6 |
| 28 wt. % aqueous ammonia | 5 |
| oleyl alcohol | 4 |
| polyoxyethylene(20) octyldodecyl ether | 17 |
| polyoxyethylene(9) oleyl ether | 4 |
| polyoxyethylene(3) tridecyl ether | 14 |
| stearyltrimethylammonium chloride | 0.5 |
| dicetyldimethylammonium chloride | 0.3 |
| polypropylene glycol 400 | 5 |
| Na sulfite anhydrate | 0.6 |
| 4Na edetate dihydrate | 0.1 |
| perfume | 0.5 |
| purified water | 21.1 |
| Total | 100 |

-continued

|  | (wt.%) |
| --- | --- |
| Second composition | |
| 35 wt. % aqueous hydrogen peroxide | 17 |
| cetyl alcohol | 2.5 |
| polyoxyethylene(2) cetyl ether | 1.2 |
| stearyltrimethylammonium chloride | 1 |
| amino-modified silicone emulsion (40 wt. %) * | 1 |
| 8-quinolinol sulfate | 0.04 |
| 75 wt. % phosphoric acid | 0.03 |
| purified water | 77.23 |
| Total | 100 |

* Same as Example 3

The first composition and the second composition were mixed at a ratio of 1:1 (by weight), to thereby prepare a composition. When used, the composition provided a weak offensive odor and favorably dyed the hair sample to a bright color tone. The texture of the hair sample after having undergone dyeing was smooth.

Example 10

An oxidation-type hair dye having the following composition was prepared, and its dyeing effect was evaluated.

|  | (wt. %) |
| --- | --- |
| First composition | |
| toluene-2, 5-diamine | 0.12 |
| p-aminophenol | 1.2 |
| m-aminophenol | 0.8 |
| p-amino-o-cresol | 0.3 |
| o-aminophenol | 0.3 |
| 2-benzyloxyethanol | 16 |
| ethanol | 2.8 |
| monoethanolamine | 6 |
| oleyl alcohol | 3 |
| polyoxyethylene(20) octyldodecyl ether | 16 |
| polyoxyethylene(9) oleyl ether | 8 |
| polyoxyethylene (3) tridecyl ether | 14 |
| isostearyl glyceryl ether | 1.5 |
| isostearyl pentaerythryl glyceryl ether | 4 |
| stearyltrimethylammonium chloride | 2 |
| Na sulfite anhydrate | 0.5 |
| ascorbic acid | 0.5 |
| chamomile extract | 0.1 |
| fucus extract | 0.01 |
| perfume | 0.5 |
| purified water | 22.37 |
| Total | 100 |
| Second composition | |
| 35 wt. % aqueous hydrogen peroxide | 17 |
| cetyl alcohol | 3 |
| glycerin | 1 |
| polyoxyethylene(2) cetyl ether | 0.5 |
| polyoxyethylene(40) cetyl ether | 0.5 |
| isostearyl pentaerythryl glyceryl ether | 2 |
| stearyltrimethylammonium chloride | 2.4 |
| amino-modified silicone emulsion (40 wt. %) * | 2 |
| 8-quinolinol sulfate | 0.04 |
| 75 wt. % phosphoric acid | 0.03 |
| purified water | 71.53 |
| Total | 100 |

* Same as Example 3

The first composition and the second composition were mixed at a ratio of 1:1.5 (by weight), to thereby prepare a composition. When used, the composition provided a weak offensive odor and favorably dyed the hair sample to a bright color tone. The texture of the hair sample after having undergone dyeing was smooth.

Example 11

An oxidation-type hair dye having the following composition was prepared, and its dyeing effect was evaluated.

|  | (wt. %) |
| --- | --- |
| First composition | |
| First composition | |
| Basic Yellow 87 | 0.2 |
| Basic Orange 31 | 0.1 |
| Basic Red 51 | 0.03 |
| 2-benzyloxyethanol | 18 |
| ethanol | 3 |
| 28 wt. % aqueous ammonia | 1 |
| monoethanolamine | 5 |
| oleyl alcohol | 3 |
| polyoxyethylene (20) octyldodecyl ether | 16 |
| polyoxyethylene (9) oleyl ether | 8 |
| polyoxyethylene (3) tridecyl ether | 14 |
| isostearyl glyceryl ether | 1.5 |
| isostearyl pentaerythryl glyceryl ether | 4 |
| stearyltrimethylammonium chloride | 2 |
| perfume | 0.5 |
| purified water | 23.67 |
| Total | 100 |
| Second composition | |
| 35 wt. % aqueous hydrogen peroxide | 17 |
| cetyl alcohol | 3 |
| glycerin | 1 |
| polyoxyethylene (2) cetyl ether | 0.5 |
| polyoxyethylene (40) cetyl ether | 0.5 |
| isostearyl pentaerythryl glyceryl ether | 2 |
| stearyltrimethylammonium chloride | 2.4 |
| amino-modified silicone emulsion (40 wt. %)* | 2 |
| 8-quinolinol sulfate | 0.04 |
| 75 wt. % phosphoric acid | 0.03 |
| purified water | 71.53 |
| Total | 100 |

*Same as Example 3

The first composition and the second composition were mixed at a ratio of 1:1.5 (by weight), to thereby prepare a composition. When used, the composition provided a weak offensive odor and favorably dyed the hair sample to a bright color tone. The texture of the hair sample after having undergone dyeing was smooth.

Example 12

A three-composition-type hair bleach having the following composition was prepared, and its bleaching effect was evaluated.

|  | (wt. %) |
| --- | --- |
| First composition (liquid) | |
| benzyl alcohol | 12 |
| ethanol | 2.7 |
| monoethanolamine | 6 |
| oleyl alcohol | 2 |
| polyoxyethylene (20) octyldodecyl ether | 18 |

-continued

|  | (wt. %) |
| --- | --- |
| polyoxyethylene (9) oleyl ether | 6 |
| polyoxyethylene (3) tridecyl ether | 15 |
| stearyltrimethylammonium chloride | 2 |
| polyethylene glycol 400 | 8 |
| liquid paraffin | 5 |
| perfume | 0.4 |
| purified water | 22.9 |
| Total | 100 |
| Second composition (liquid) | |
| 35 wt. % aqueous hydrogen peroxide | 17 |
| 8-quinolinol sulfate | 0.04 |
| 75 wt. % phosphoric acid | 0.02 |
| purified water | 82.94 |
| Total | 100 |
| Third composition (powder) | |
| sodium persulfate | 10 |
| potassium persulfate | 16 |
| ammonium persulfate | 26 |
| sodium metasilicate anhydrate | 20 |
| sodium silicate | 17.8 |
| silicic anhydride | 1 |
| sodium stearate | 5 |
| sodium lauryl sulfate | 1 |
| 4Na edetate unhydrate | 1 |
| β-cyclodextrin | 0.2 |
| xantan gum | 1 |
| Na carboxymethyl cellulose | 1 |
| Total | 100 |

The first composition, the second composition, and the third composition were mixed at proportions of 1:1.5:0.5 (by weight), to thereby prepare a composition. When used, the composition provided a weak offensive odor and excellent bleach power. The texture of the hair sample after having undergone bleaching was smooth.

What is claimed is:

1. A hair bleach or dye composition, comprising:
   at least two separate components of:
   a first aqueous alkali component containing an alkali agent (C) in an amount of 0.1–10 wt % based on the entire composition, and
   a second aqueous oxidation component containing an oxidizing agent (D) in an amount corresponding in effect to 0.1–12 wt % of hydrogen peroxide; the composition further comprising:
   (A) an organic solvent having a partition coefficient (octanol-water) (log P) at 25° C. of 0.3–6 and a molecular weight of 200 or less, in at least one of the first aqueous alkali and second aqueous oxidation components such that the total amount of component (A) ranges from 1–70 wt % of the entire composition;
   (B) an organic solvent having a partition coefficient (octanol-water) (log P) at 25° C. of less than 0.3, in at least one of the first aqueous alkali and second aqueous oxidation components such that the total amount of component (B) ranges from 0–8 wt % of the entire composition, but less than the amount of component (A);
   (E) water in an amount of 20–55 wt % of the entire composition; and
   a saturated or unsaturated $C_{12}$–$C_{22}$ linear or branched monohydric alcohol (I) in at least one of the first aqueous alkali or second aqueous oxidation components in an amount ranging from 0.1–20 wt % based on the entire composition, the hair bleach composition, upon admixture of the first aqueous alkali and second aqueous oxidation components upon use, having a pH of 7.5–12.

2. The hair bleach or dye composition according to claim 1, wherein the first aqueous alkali component contains ammonia in an amount of 0–3 wt % based on the entire composition.

3. The hair bleach or dye composition according to claim 1, which further comprises a third oxidizing component of a persulfate salt in an amount of 1–30 wt % based on the entire composition.

4. The hair bleach or dye composition according to claim 1, which further comprises a cationic surfactant component (F) in at least one of the first aqueous alkali and second aqueous oxidation components in an amount ranging from 0.01–10 wt %.

5. The hair bleach or dye composition according to claim 1, which further comprises color developing and coupling substances in combinations of two or more substances in respective amounts of 0.01–5 wt % based on the entire composition or a direct dye.

6. The hair bleach or dye composition according to claim 1, which further comprises a polyoxyalkylene compound as component (J) in at least one of the first aqueous alkali and second aqueous oxidation components selected from the group consisting of polyalkylene glycol having a total polycondensation number of $C_2$–$C_4$ oxyalkylene groups of 4 or more, polyalkylene glycol alkyl ($C_{1-4}$) ethers, polyalkylene glycol glyceryl ethers, polyalkylene glycol pentaerythritol alkylene ethers, polyalkylene glycoltrimethylolpropane ethers and polyalkylene glycol alkylene glycoyl ethers in at least one of the first and second components in an amount ranging from 0.1–20 wt % based on the entire composition.

7. The hair bleach or dye composition according to claim 1, which further comprises at least two nonionic surfactants of different HLB values of which one is a hydrophilic nonionic surfactant (K) having an HLB value of 10–20 and another is an oleophilic nonionic surfactant (L) having an HLB value of 1–10, the surfactants incorporated in the first aqueous alkali component or the second aqueous oxidation component or both of the components.

8. The hair bleach or dye composition according to claim 7, wherein the hydrophilic nonionic surfactant is a polyoxyethylene alkyl ether or an alkyl glycoside.

9. The hair bleach or dye composition according to claim 7, wherein the oleophilic nonionic surfactant is a polyoxyethylene alkyl ether having an HLB of 1–10, a polyoxyethylene polypropylene alkyl ether, an alkyl glyceryl ether, alkyl glyceryl pentaerythritol ether, an alkyl diglyceryl ether or an alkyl triglyceryl ether, all having an HLB value of 1–10.

10. A hair bleach or dye composition, comprising:
at least two separate components of:
  a first aqueous alkali component containing an alkali agent (C) in an amount of 0.1–10 wt % based on the entire composition, and
  a second aqueous oxidation component containing an oxidizing agent (D) in an amount corresponding in effect to 0.1–12 wt % of hydrogen peroxide; the composition further comprising:
    (A) an organic solvent having a partition coefficient (octanol-water) (log P) at 25° C. of 0.3–6 and a molecular weight of 200 or less, in at least one of the first aqueous alkali and second aqueous oxidation components such that the total amount of component (A) ranges from 1–70 wt % of the entire composition;
    (B) an organic solvent having a partition coefficient (octanol-water) (log P) at 25 C. of less than 0.3, in at least one of the first aqueous alkali and second aqueous oxidation components such that the total amount of component (B) ranges from 0–8 wt % of the entire composition, but less than the amount of component (A);
    (E) water in an amount of 20–70 wt % of the entire composition;
    (F) a cationic surfactant in at least one of the first aqueous alkali and second aqueous oxidation components in an amount of 0.01–10 wt % based on the entire bleach composition; and
a saturated or unsaturated $C_{12}$–$C_{22}$ linear or branched monohydric alcohol (I) in at least one of the first aqueous alkali or second aqueous oxidation components in an amount ranging from 0.1–20 wt % based on the entire composition, the hair bleach composition, upon admixture of the first aqueous alkali and second aqueous oxidation components upon use, having a pH of 7.5–12.

11. The hair bleach or dye composition according to claim 10, wherein the first aqueous alkali component contains ammonia in an amount of 0–3 wt % based on the entire composition.

12. The hair bleach or dye composition according to claim 10, which further comprises a third oxidizing component of a persulfate salt in an amount of 1–30 wt % based on the entire composition.

13. The hair bleach or dye composition according to claim 10, which further comprises color developing and coupling substances in combinations of two or more substances in respective amounts of 0.01–5 wt % based on the entire composition.

14. The hair bleach or dye composition according to claim 10, which further comprises a polyoxyalkylene compound as component (J) in at least one of the first aqueous alkali or second aqueous oxidation components selected from the group consisting of polyalkylene glycol having a total polycondensation number of $C_2$–$C_4$ oxyalkylene groups of 4 or more, polyalkylene glycol alkyl ($C_{1-4}$) ethers, polyalkylene glycol glyceryl ethers, polyalkylene glycol pentaerythritol alkylene glycol ethers, polyalkylene glycoltrimethylolpropane ethers and polyalkylene glycol alkylene glycol ethers in at least one of the first aqueous alkali and second aqueous oxidation components in an amount ranging from 0.1–20 wt % based on the entire composition.

15. The hair bleach or dye composition according to claim 10, which further comprises at least two nonionic surfactants of different HLB values of which one is a hydrophilic nonionic surfactant (K) having an HLB value of 10–20 and another is an oleophilic nonionic surfactant (L) having an HLB value of 1–10, the surfactants incorporated in the first aqueous alkali component or the second aqueous oxidation component or both of the components.

16. The hair bleach or dye composition according to claim 15, wherein the hydrophilic nonionic surfactant is a polyoxyethylene alkyl ether or an alkyl glycoside.

17. The hair bleach or dye composition according to claim 15, wherein the oleophilic nonionic surfactant is a polyoxyethylene alkyl ether having an HLB of 1–10, a polyoxyethylene polypropylene alkyl ether, an alkyl glyceryl ether, alkyl glyceryl pentaerythritol ether, an alkyl diglyceryl ether or an alkyl triglyceryl ether, all having an HLB value of 1–10.

* * * * *